(12) United States Patent
Wilkinson

(10) Patent No.: US 7,201,721 B2
(45) Date of Patent: Apr. 10, 2007

(54) MEASURING TISSUE MOBILITY

(75) Inventor: Malcolm Howard Wilkinson, Forest Hill (AU)

(73) Assignee: Pulmosonix Pty Ltd (AU)

( * ) Notice: Subject to any disclaimer, the term of this patent is extended or adjusted under 35 U.S.C. 154(b) by 140 days.

(21) Appl. No.: 11/001,959

(22) Filed: Dec. 2, 2004

(65) Prior Publication Data
US 2005/0085747 A1      Apr. 21, 2005

Related U.S. Application Data

(63) Continuation of application No. PCT/AU03/00691, filed on Jun. 3, 2003.

(30) Foreign Application Priority Data
Jun. 3, 2002   (AU) .......................... PS2741

(51) Int. Cl.
*A61B 5/00*     (2006.01)
(52) U.S. Cl. .................................................. 600/552
(58) Field of Classification Search ................ 600/552, 600/438, 442, 443, 437, 587, 553; 73/597–599
See application file for complete search history.

(56) References Cited

U.S. PATENT DOCUMENTS

| 5,836,891 A | 11/1998 | DiMarogonas |
| 5,919,139 A | 7/1999 | Lin |

FOREIGN PATENT DOCUMENTS

| RU | 2 177 759 | 1/2001 |
| WO | WO 97/00643 | 1/1997 |
| WO | WO 00/44281 | 8/2000 |
| WO | WO 01/80742 | 11/2001 |

*Primary Examiner*—Max F. Hindenburg
*Assistant Examiner*—Brian Szmal
(74) *Attorney, Agent, or Firm*—Hahn Loeser & Parks LLP; Michael H. Minns

(57) ABSTRACT

A method of measuring tissue mobility includes applying an oscillatory force to a region of tissue and measuring the velocity with which the tissue moves in response to the applied force. Tissue mobility is then determined by a ratio of the tissue velocity to the applied force.

12 Claims, 2 Drawing Sheets

MEASURING TISSUE MOBILITY

This application is a continuation of International application PCT/AU03/00691, Jun. 3, 2003, the disclosure of which is hereby incorporated by reference.

FIELD OF THE INVENTION

This invention relates to a method of measuring tissue mobility. It relates particularly but not exclusively to a method of measuring tissue mobility by applying a oscillatory force to a region of tissue and measuring the velocity with which the tissue moves in response to the oscillatory force, and a system of doing the same.

BACKGROUND TO THE INVENTION

Percussion has been used routinely during chest examination for many years. Using this technique, a trained clinician is able to distinguish underlying clinical abnormalities by observing the characteristic sounds radiated in response to a sharp tap to the body surface at the point being examined. Using this technique, a great deal of information can be obtained which relates to the condition of the lung, abdominal and other organs. Clinical abnormalities such as complete lung collapse (pneumo-thorax), regional lung collapse (atelectasis) and gas trapping in the bowel can be detected.

When percussion is performed over different areas of the body, the sound radiated is variously described as dull (over the liver) or stony dull (associated with a pleural effusion) or as resonant (over the lung) or hyper-resonant (over the bowel). The mechanism by which the variation in radiated sound occurs is not fully understood. However, it seems likely that the observed "resonance" following percussion of the lung, bowel or other tissue results from the presence of gas, and that the high compliance of the gas decreases the mechanical damping of the overlying tissue. This has the effect of increasing the mobility of the overlying tissue and allowing it to resonate following the percussive tap. Conversely, where the sub-tissue environment contains principally fluid, the tissue damping will be increased and the mobility decreased, resulting in a "duller" percussive sound.

In infants, the tissue in the chest is highly compliant and percussion is more difficult to perform. This is in part due to the fact that the force delivered in each tap must be limited to avoid causing injury to the infant. Further, the adult finger that is used both as a coupling device and sounding board between the infant's body surface and the percussing finger is too large to be used in tiny infants. Currently, no method exists which can be safely applied to the newborn infant and which provides useful information similar to that which is obtained using traditional percussive techniques which are applicable for adults.

SUMMARY OF THE INVENTION

According to a first aspect of the invention, there is provided a method of measuring tissue mobility comprising the steps of:
(a) applying an oscillatory force to a region of tissue using a vibrating mass having an oscillatory velocity $u_m$ and
(b) determining an oscillatory velocity $u_t$ with which the tissue moves in response to the applied force;
  wherein tissue mobility is determined by a ratio of the tissue velocity $u_t$ to the velocity of the vibrating mass, $u_m$.

The oscillatory force may be constant, or its frequency may vary over a period of time. Accordingly, the oscillatory force may consist of a series of discrete frequencies applied sequentially, or it may correspond to pseudo-random noise or white noise wherein a range of frequencies are applied simultaneously.

In a preferred embodiment, the oscillatory force is applied using a vibrating mass which is set in motion with a velocity, $u_m$. The vibrating mass may be set in motion using an electromagnetic driver which is coupled to the tissue via a coupling device. In such an embodiment, the mobility of the tissue can be determined using:

$$z_t(f) = \frac{1}{2\pi f \left\{ \frac{u_m}{u_t} m_v + m_f \right\}}$$

where $u_t$ is the oscillatory velocity of the tissue which is coupled to the vibrating mass;

$m_v$ is the mass of the vibrating mass; and $m_f$ is the mass of the coupling device.

In an alternative embodiment, tissue transfer mobility may be determined. In such an embodiment, a force, oscillatory or otherwise, may be applied to a region of tissue and the velocity with which the tissue moves in response to that force is measured at a site which is spatially distinct from the point of force application. Such a measurement may be useful for determining joint mobility in humans or other animals.

According to a second aspect of the present invention, there is provided apparatus for measuring mobility of a region of tissue comprising:
(a) a force generator driving a vibrating mass with an oscillatory velocity, $u_m$ for application of an oscillatory force to a region of tissue;
(b) a tissue velocity determiner producing a tissue velocity signal $u_t$ which corresponds to the velocity with which the tissue moves in response to the applied oscillatory force; and
(c) a processor processing the tissue velocity signal $u_t$ and the vibrating mass velocity signal, $u_m$;
  wherein the tissue's mobility is determined using a ratio of the tissue velocity, $u_t$ to the velocity of the vibrating mass, $u_m$.

A single frequency may be applied over a period of time, or the frequency may be varied sequentially. Alternatively many different frequencies may be applied simultaneously in the form or pseudo-random noise or white noise. The oscillatory force generator may be a magnet supported within a set of concentric field coils, the field coils being driven with a swept frequency current. However, any other appropriate force-generating device suitable for generating an oscillatory force could be used.

It is preferred that the oscillatory force generator is a vibrating mass which is set in motion with a velocity, $u_m$. This may be achieved using an electromagnetic driver as described, which is coupled to the tissue using a coupling device. Accordingly, the mobility of the tissue can be determined using the equation:

$$z_t(f) = \frac{1}{2\pi f \left\{ \frac{u_m}{u_t} m_v + m_f \right\}}$$

where $u_t$ is the velocity of the tissue which is coupled to the vibrating mass;

$m_v$ is the mass of the vibrating mass; and $m_f$ is the mass of the coupling device.

According to a third aspect of the present invention, there is provided a data structure comprising:

(a) a first field containing data representing a velocity of a vibrating mass;

(b) a second field containing data representing a velocity of tissue; and (c) a third field containing data representing tissue mobility derived from the first field and the second field.

In another embodiment, the apparatus may be used to determine tissue transfer mobility, wherein the oscillatory velocity at which the tissue moves in response to the applied force is measured at a location which is spatially distinct from the region of tissue to which the oscillatory force is applied.

The apparatus may also include a display device for displaying a representation of mobility of the region of tissue, wherein the representation of mobility includes a graph of mobility versus frequency.

The character of the sound which is radiated following percussion is determined, at least in part, by the mechanical mobility and resonant frequency of the tissue interface at the percussion site. This is, in turn, influenced by the damping effect of underlying fluid or gas. Accordingly, the apparatus of the present invention, which is designed to measure mobility as a function of frequency, is likely to be of clinical value.

The present invention provides an advantage in that it requires the use of a smaller peak force than is applied with the impulse method for determining tissue mobility. Accordingly, it is safer for use in infants. A further advantage of the present invention over traditional percussive techniques is that it is less dependent on the clinical experience of the practitioner and does not require a quiet environment.

BRIEF DESCRIPTION OF THE DRAWINGS

The invention will herein after be described in greater detail by reference to the attached drawings. It is to be understood that the particularity of the drawings does not supersede the generality of the preceding description of the invention.

DETAILED DESCRIPTION

In principle, mobility can be measured by applying an impulsive force to tissue and examining the temporal change in velocity that follows. However, equivalent information can also be obtained by using a smaller oscillatory force. This is preferable for testing tissue mobility in infants, as the highly compliant tissue of an infant's chest can withstand low magnitude oscillating forces, whereas single impulse forces which are applied in adult percussive techniques are likely to cause injury.

Figure 1:
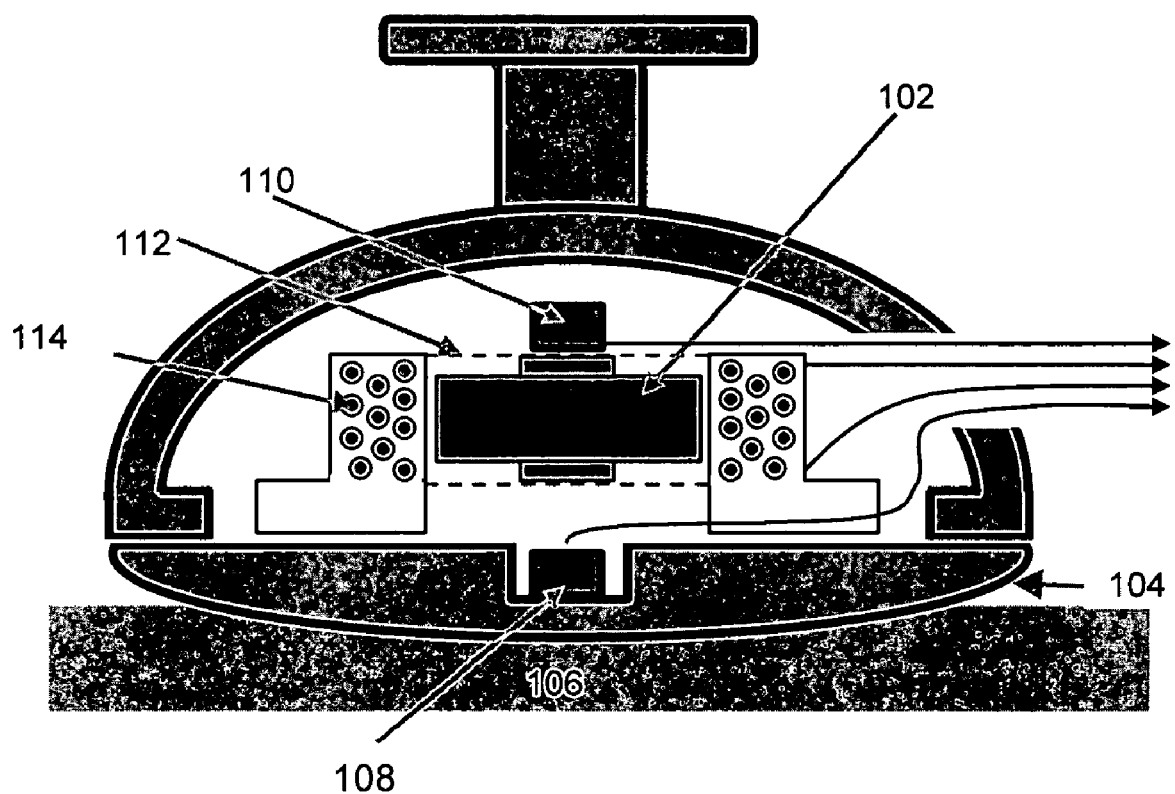
FIG. 1 illustrates a transducer for use in an embodiment of the invention where an oscillatory force is applied to the tissue.

In the preferred embodiment illustrated in FIG. 1, a small oscillatory force is applied to the surface of the tissue using a broad range of frequencies which are applied for a burst of approximately 5 seconds, although the burst of frequencies may last for a longer or a shorter period. Mobility can then be determined at each frequency by measuring simultaneously the applied oscillatory force and the resultant tissue velocity. The frequencies may be applied sequentially, or simultaneously in the form of pseudo-random or "white" noise. When pseudo-random frequencies are used, a range of frequencies are applied at once. Accordingly, the mobility of the tissue can be determined more quickly.

Referring to the illustration in FIG. 1, a vibrating mass 102 of mass m is set in motion using an electromagnetic driver. The force generated by the acceleration of vibrating mass 102 appears as a reactive force. This reactive force is coupled via coupling device 104 to tissue 106, the mobility of which is being tested. In the example illustrated in FIG. 1, coupling device 104 is a light-weight frame, the mass of which includes the mass of field coils 114 which are used to excite vibrating mass 102. Tissue velocity transducer 108 is used to measure the velocity, $u_t$, of tissue 106 which is in contact with frame 104. Vibrating mass velocity transducer 110 is used to measure the velocity, $u_m$, of the vibrating mass. However, tissue velocity transducer 108 and vibrating mass velocity transducer 110 may measure acceleration from which a value for velocity may be derived mathematically.

In such an embodiment, where an oscillatory force is applied to tissue 106, it can be shown that the magnitude of the combined mobility of tissue 106 and frame 104, as a function of frequency denoted by $z_c(f)$ can be determined using the following expression.

$$z_c(f) = \frac{u_t}{F_{OSC}} = \frac{u_t}{2\pi f u_m m_v} \qquad \text{(equation 1)}$$

where: $F_{osc}$ is the oscillatory force applied to tissue 106;

$m_v$ is the mass of vibrating mass 102; and $f$ is the frequency of oscillation.

By using the known mass of frame 104, it is possible to deduce the mobility of tissue 106 alone, denoted by $z_t(f)$ using the following expression:

$$z_t(f) = \frac{1}{2\pi f \left\{ \frac{u_m}{u_t} m_v + m_f \right\}} \qquad \text{(equation 2)}$$

where: $m_f$ is the mass of frame 104.

In general $z_t(f)$ is a complex value and its phase varies with frequency.

Energy is stored in tissue as a consequence of its mass and stiffness. This results in the presence of resonant frequencies which may then be used to characterize different parts of the body's surface. Accordingly, analysis of the magnitude and phase of mobility $z_t(f)$ as a function of frequency can give information about the nature of the tissue under test. Therefore, periodically measuring tissue mobility and monitoring the changes in tissue mobility with time may indicate the presence or development of underlying disease and/or may be used to identify changes in the fluid or gas content of the underlying tissue.

In the embodiment of FIG. 1, reactive mass 102 is a cylindrical magnet forming part of a motor assembly. Reactive mass 102 is suspended on two flexible spider supports 112 within a concentric set of field coils 114. Field coils 114 are driven with a swept frequency current so that the reactive mass 102 is set in motion at the driving frequency. The reactive force generated by the motion of the reactive mass 102 is coupled to tissue 106 via frame 104 as previously described.

Figure 2:
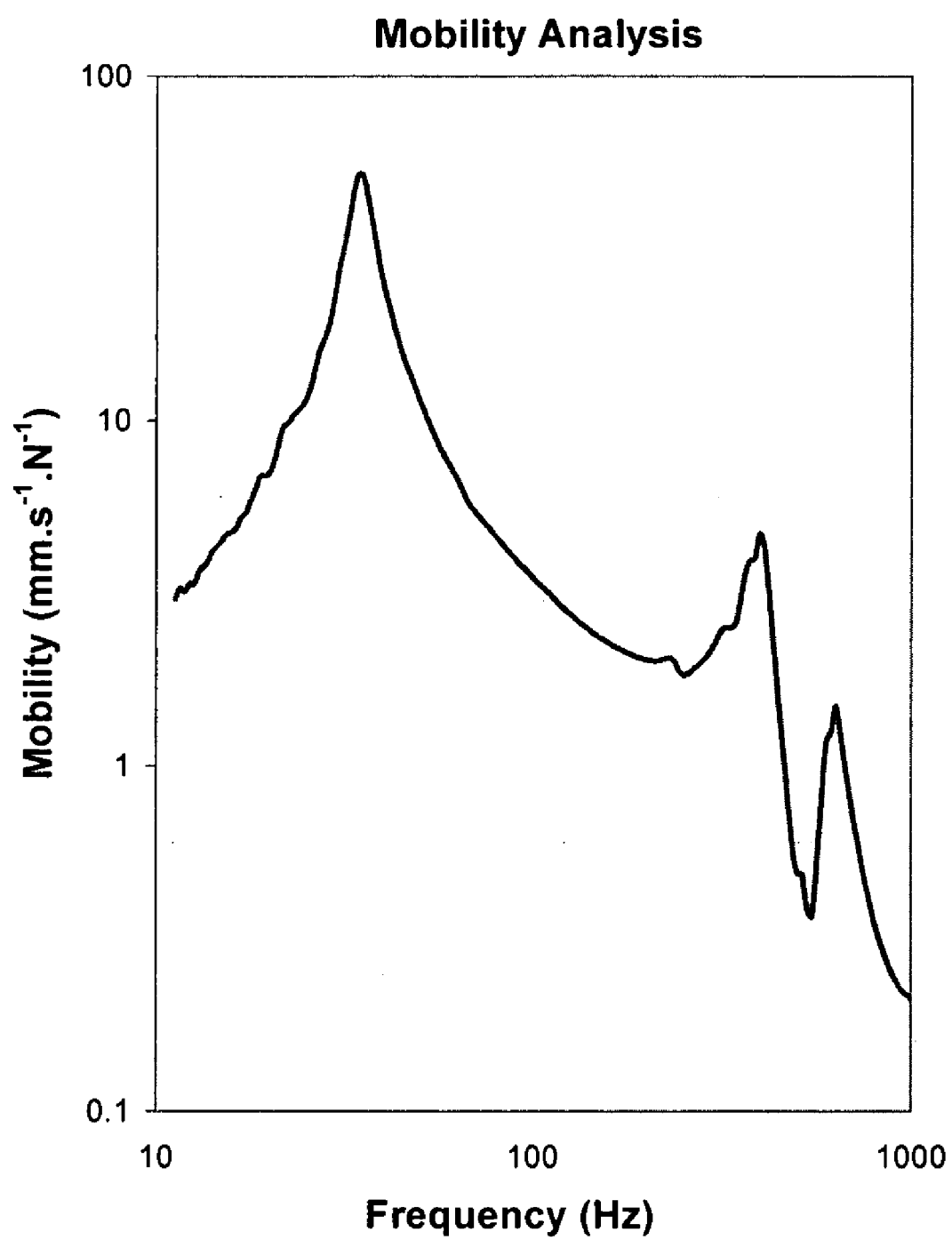
FIG. 2 indicates tissue mobility in a plot of Mobility ($mm \cdot s^{-1} \cdot N^{-1}$) against Frequency (Hz).

In the embodiment of FIG. 1, tissue velocity transducer 108 and vibrating mass transducer 110 are accelerometers. The output from these accelerometers is sent to a processor where the magnitude and phase of the tissue mobility is calculated using equation 2 and then displayed. A typical display of values which are obtained in a mobility measurement in accordance with the present invention is shown in FIG. 2.

It is to be understood that a number of other motor types could be used to provide vibrating mass 102. These motor types include but are not limited to electrostatic and pneumatic types. Further, the size of the part of the apparatus which contacts the tissue is readily scalable for different applications in both pediatric and adult medicine, depending on the types of transducers used. Moreover, it is to be understood that, by characterizing the motor or by using electronic feedback to regulate the velocity of vibrating mass 102, it is possible to eliminate vibrating mass velocity transducer 110, thereby simplifying the apparatus. In a further adaptation, tissue velocity transducer 108 may be made mobile so that the mobility of tissue at one part of the body can be measured in response to vibration at a spatially different part of the body, providing a measurement of tissue transfer mobility.

The present invention may also be used to measure and/or analyze tissue impedance, $Z_t(f)$, where impedance is the inverse of tissue mobility, $z_t(f)$, as shown in equation 3.

$$Z_t(f) = \frac{1}{z_t(f)} \qquad \text{(equation 3)}$$

Various alterations, additions and/or modifications may be made to the parts previously described without departing from the ambit of the present invention.

What is claimed is:

1. A method of measuring tissue mobility comprising the steps of:
   (a) applying an oscillatory force to a region of tissue using a vibrating mass having an oscillatory velocity $u_m$; and
   (b) determining an oscillatory velocity $u_t$ with which the tissue moves in response to the applied force;
      wherein tissue mobility is determined by a ratio of the tissue velocity $u_t$ to the velocity of the vibrating mass, $u_m$.

2. A method of measuring tissue mobility according to claim 1 wherein the frequency of the oscillatory force is varied over a period of time.

3. A method of measuring tissue mobility according to claim 1 wherein the oscillatory force corresponds to pseudorandom noise or white noise.

4. A method of measuring tissue mobility according to claim 1 wherein the force is applied using a vibrating mass which is set in motion, with oscillatory velocity $u_m$, using an electromagnetic driver which is coupled to the tissue via a coupling device.

5. A method of measuring tissue mobility according to claim 4, wherein the mobility of the tissue, $z_t(f)$ is given by:

$$z_t(f) = \frac{1}{2\pi f \left\{ \frac{u_m}{u_t} m_v + m_f \right\}}$$

where $m_v$ is the mass of the vibrating mass; and
$m_f$ is the mass of the coupling device.

6. A method of measuring tissue mobility according to claim 1 wherein the velocity at which the tissue moves in response to the applied force is determined at a location which is spatially distinct from the region of tissue to which the force is applied.

7. A method of measuring tissue mobility according to claim 1 comprising the additional step of providing a visual representation of the velocity at which the tissue moves in response to the applied force.

8. Apparatus for measuring mobility of a region of tissue comprising:
   (a) a force generator driving a vibrating mass with an oscillating velocity $u_t$ for application of an oscillatory force to a region of tissue;
   (b) a tissue velocity determiner producing a tissue velocity signal $u_t$ which corresponds to the velocity with which the tissue moves in response to the applied oscillatory force; and
   (c) a processor processing the tissue velocity signal $u_t$ and the vibrating mass velocity signal $u_m$;
      wherein the tissue's mobility is determined using a ratio of the tissue velocity $u_t$ to the velocity of the vibrating mass, $u_m$.

9. Apparatus for measuring tissue mobility according to claim 8 wherein the force generator is a vibrating mass which is set in motion with an oscillatory velocity $u_m$, using an electromagnetic driver which is coupled to the tissue via a coupling device.

10. Apparatus for measuring tissue mobility according to claim 9, wherein the mobility of the tissue, $z_t(f)$ at a frequency $f$ is given by:

$$z_t(f) = \frac{1}{2\pi f \left\{ \frac{u_m}{u_t} m_v + m_f \right\}}$$

where:
$m_v$ is the mass of the vibrating mass; and
$m_f$ is the mass of the coupling device.

11. Apparatus for measuring tissue mobility according to claim 8 wherein the force generator applies an oscillatory force to a region of tissue which is spatially distinct from the location of the tissue velocity determining means.

12. Apparatus for measuring tissue mobility according to claim 10 further comprising a display device for displaying a representation of mobility of the region of tissue, wherein the representation of mobility includes a graph of mobility versus frequency.

* * * * *